United States Patent [19]
Tucker et al.

[11] Patent Number: 6,013,856
[45] Date of Patent: *Jan. 11, 2000

[54] TERMINALLY STERILIZED OSTEOGENIC DEVICES AND PREPARATION THEREOF

[75] Inventors: Marjorie M. Tucker, Holliston; David C. Rueger, Southborough; Kuber T. Sampath, Holliston, all of Mass.

[73] Assignee: Stryker Corporation, Hopkinton, Mass.

[*] Notice: This patent is subject to a terminal disclaimer.

[21] Appl. No.: 09/159,535

[22] Filed: Sep. 23, 1998

Related U.S. Application Data

[60] Continuation of application No. 08/881,307, Jun. 24, 1997, which is a division of application No. 08/478,452, Jun. 7, 1995, Pat. No. 5,674,292.

[51] Int. Cl.$^7$ ........................................................ A61F 2/10
[52] U.S. Cl. ................................................................ 623/16
[58] Field of Search .................................. 623/11, 16, 17, 623/18, 19, 20, 21, 22, 23

[56] References Cited

U.S. PATENT DOCUMENTS

| | | |
|---|---|---|
| 4,394,370 | 7/1983 | Jeffries . |
| 4,578,384 | 3/1986 | Hollinger . |
| 4,703,108 | 10/1987 | Silver et al. . |
| 4,865,602 | 9/1989 | Smestad et al. . |
| 4,968,590 | 11/1990 | Kuberasampath et al. . |
| 5,011,691 | 4/1991 | Oppermann et al. . |
| 5,024,841 | 6/1991 | Chu et al. . |
| 5,035,715 | 7/1991 | Smestad et al. . |
| 5,108,753 | 4/1992 | Kuberasampath et al. . |
| 5,123,925 | 6/1992 | Smestad et al. . |
| 5,171,579 | 12/1992 | Ron et al. . |
| 5,266,683 | 11/1993 | Oppermann et al. . |
| 5,385,887 | 1/1995 | Yim et al. ................................. 514/12 |
| 5,514,180 | 5/1996 | Heggeness et al. ....................... 623/17 |
| 5,520,923 | 5/1996 | Tjia et al. ................................. 623/16 |
| 5,563,124 | 10/1996 | Damien et al. ........................... 623/16 |
| 5,597,897 | 1/1997 | Ron et al. ................................ 530/350 |

FOREIGN PATENT DOCUMENTS

| | | |
|---|---|---|
| 0 361 896 A3 | 4/1990 | European Pat. Off. . |
| 0 567 391 A1 | 10/1993 | European Pat. Off. . |
| WO 93/00050 | 1/1993 | WIPO . |
| WO 93/16739 | 9/1993 | WIPO . |

OTHER PUBLICATIONS

Cheung et al. (1990) "The effect of γ–Irradiation on Collagen Molecules, Isolated α–Chains, and Crosslinked Native Fibers" *Journal of Biomedical Materials Research* 24: 581–589.

Chu et al. (1983) "The Effect of Gamma Irradiation on the Enzymatic Degradation of Polyglycolic Acid Absorbable Sutures" *Journal of Biomedical Materials Research* 17: 1029–1040.

Ijiri, et al. (1994) "Effect of Sterilization on Bone Morphogenetic Protein" *Journal of Orthopaedic Research* 12: 628–636.

Katz et al. (1990) "Radiation–Sterilized Insoluble Collagenous Bone Matrix is a Functional Carrier of Osteogenin for Bone Induction" *Calcified Tissue International* 47: 183–185.

Liu et al. (1989) "The Effect of Gamma Irradiation on Injectable Human Amnion Collagen" *Journal of Biomedical Materials Research* 23: 883–894.

Munting et al. (1988) "Effect of Sterilization on Osteoinduction" *Acta Orthop Scand* 59:34–38.

Puolakkainen et al.(1993) "The Effect of Sterilization on Transforming Growth Factor β Isolated from Demineralized Human Bone" *Transfusion* 33: 679–685.

Raptopoulou–Gigi et al. (1977) "Antimicrobial Proteins in Sterilized Human Milk" *British Medical Journal* 1: 12–14.

Reid (1995) "Gamma Processing Technology: An Alternative Technology for Terminal Sterilization of Parenterals" *PDA Journal of Pharmaceutical Science & Technology* 49: 83–89.

Soboleva et al. (1981) "Radiation Resistivity of Frozen Insulin Solutions and Suspensions" *International Journal of Applied Radiation and Isotopes* 32: 753–756.

Schwartz et al. (1988) "Irradiation–Sterilization of Rat Bone Matrix Gelatin" *Acta Orthop Scand* 59: 165–167.

Wientroub et al. (1988) "Influence of Irradiation on the Osteoinductive Potential of Demineralized Bone Matrix" *Calcified Tissue International* 42: 255–260.

Sue et al. (Sep. 1995) Pharm. Res. Suppl V12, No. 9 p S 87, Abstract–No. 2035 for AAPS Tenth Annual Meeting and Exposition, Nov. 5–9, 1995.

Copy of International Search Report for counterpart application PCT/US96/10377.

*Primary Examiner*—Jeffrey A. Smith
*Assistant Examiner*—Eduardo C. Robert
*Attorney, Agent, or Firm*—Testa, Hurwitz & Thibeault LLP

[57] ABSTRACT

Disclosed are terminally sterilized osteogenic devices for implantation into a mammal. The devices contain a combination of a biologically active osteogenic protein and an insoluble carrier which after being combined are sterilized by exposure to ionizing radiation, for example, by exposure to gamma rays or an electron beam. The terminally sterilized devices of the invention are characterized in that they induce bone formation following implantation into a mammal. Also disclosed is a method for inducing bone formation in a mammal by implanting a terminally sterilized device of the invention into a preselected locus in a mammal. Also disclosed is a method for preparing the terminally sterilized device of the invention.

34 Claims, 1 Drawing Sheet

TERMINALLY STERILIZED OSTEOGENIC DEVICES AND PREPARATION THEREOF

REFERENCE TO RELATED APPLICATION

This application is a continuation of U.S. Ser. No. 08/881,307, filed Jun. 24, 1997, which is a divisional of U.S. Ser. No. 08/478,452, filed Jun. 7, 1995, now U.S. Pat. No. 5,674,292, the disclosures of which are incorporated by reference herein.

TECHNICAL FIELD OF THE INVENTION

This invention relates generally to the field of osteogenic devices and, more particularly, to terminally sterilized osteogenic devices which are capable of inducing bone formation following implantation into a mammal

BACKGROUND OF THE INVENTION

Therapeutic devices, and more specifically, osteogenic devices, typically are sterilized prior to implantation in an intended recipient. Sterilization is required to ensure that the devices do not introduce potential pathogens, or other biologically infectious agents into the intended recipient. Osteogenic devices comprising an osteogenic protein in combination with an insoluble carrier material are useful for inducing bone formation at a preselected locus, e.g., at a site of a bone fracture, in a mammal. Heretofore, the carrier material and osteogenic protein typically have been sterilized separately and then combined to produce a sterile implantable device. This method, however, cannot guarantee the sterility of the resulting device.

The most desirable method for sterilizing a device comprising two or more components is by a process, referred to in the art as "terminal sterilization". By this process, the device is sterilized following formulation, i.e., after all the components have been combined with one another in the device. A variety of physical or chemical methods have been developed for use in terminal sterilization and include, for example, exposure to chemicals or heat, or exposure to ionizing or non-ionizing radiation. These methods, however, can have inherent problems.

For example, chemical reagents useful in chemical sterilization, or the reaction byproducts, can be harmful to the intended recipient. Accordingly, such chemicals must be removed prior to implantation of the devices. Ethylene oxide and formaldehyde are reagents commonly used as sterilization reagents. However, both are alkylating agents and therefore can modify and inactivate biologically active molecules. In addition, both of these chemicals are carcinogens and mutagens (Davis et al., (1973) "*Microbiology,* 2nd Ed.", Harper and Row, Publishers). Similarly, where the device requires a biologically active protein, exposing the device to elevated temperatures is not desirable because the proteins can be denatured and subsequently inactivated by exposure to heat. Although the sterilization of objects by exposure to ionizing and non-ionizing radiation obviates the necessity of adding potentially toxic chemicals, the radiation energy and/or its byproducts, including oxygen free radicals, are competent to modify protein conformation and so can damage or inactivate the protein, In addition, exposure of some medically important polymers, for example, as polyurethane or polymethylmethacrylate to gamma radiation can result in immediate and long term physical changes to the polymer.

It is therefore an object of this invention to provide a terminally sterilized osteogenic device which, when implanted at a preselected locus in a mammal, is capable of producing bone at the locus. Another object is to provide a general process for terminally sterilizing osteogenic devices without compromising the biological activity and/or biocompatibility of the device. Another object of the invention is to provide a method of inducing bone formation at a preselected locus in a mammal using a terminally sterilized device of the invention.

These and other objects and features of the invention will be apparent from the description, drawings, and claims which follow.

SUMMARY OF THE INVENTION

It now has been discovered that a terminally sterilized therapeutic device, specifically an osteogenic device, comprising a biologically active protein, for example, an osteogenic protein, in combination with an insoluble carrier material, when sterilized by exposure to ionizing radiation is capable of inducing bone and/or cartilage formation when implanted into a mammal. The finding is unexpected as it is known that exposure of biologically active proteins to ionizing radiation can result in chemical modification and inactivation of the protein.

In its broadest aspect, the invention provides a terminally sterilized osteogenic device for implantation into a mammal which, when implanted into the mammal, induces bone and/or cartilage formation. The device is produced by the steps of (a) combining an insoluble carrier and a biologically active osteogenic protein to form an osteogenic device, and then (b) exposing the combination of step (a) to ionizing radiation under conditions to sterilize the device while maintaining biological activity of the osteogenic protein. The resulting sterile device is characterized in that it has been terminally sterilized but yet is capable of inducing bone and/or cartilage formation following implantation into the mammal.

The term, "sterilization" as used herein, refers to an act or process using either physical or chemical means for eliminating substantially all viable organisms, especially microorganisms, viruses and other pathogens, associated with an osteogenic device. As used herein, sterilized devices are intended to include devices achieving a sterility assurance level of $10^{-6}$, as determined by FDA (Federal Drug Administration) standards. The term, "terminal sterilization" as used herein, refers to the last step in the fabrication of the device of the invention wherein the insoluble carrier material is sterilized after being combined with the osteogenic protein. The term "ionizing radiation" as used herein, refers to particles or photons that have sufficient energy to produce ionization directly in their passage through a substance, e.g., the therapeutic device contemplated herein.

The term, "osteogenic device" as used herein, refers to any device having the ability, when implanted into a mammal, to induce bone formation. The device described herein also is competent to induce articular cartilage formation when implanted at an avascular site in a mammal, such as at the surface of subchondral bone in a synovial joint environment. As used herein, the term "bone" refers to a calcified (mineralized) connective tissue primarily comprising a composite of deposited calcium and phosphate in the form of hydroxyapatite collagen (predominantly Type I collagen) and bone cells, such as osteoblasts, osteocytes and osteoclasts, as well as to the bone marrow tissue which forms in the interior of true endochondral bone.

As used herein, the term "cartilage" refers to a type of connective tissue that contains chondrocytes embedded in an extracellular network comprising fibrils of collagen (predominantly Type II collagen along with other minor types, e.g. Types IX and XI), various proteoglycans (e.g., chondroitin sulfate, keratan sulfate, and dermatan sulfate proteoglycans), other proteins, and water. "Articular cartilage" refers to hyaline or articular cartilage, an avascular, non-mineralized tissue which covers the articulating surfaces of bones in joints and allows movement in joints without direct bone-to-bona contact, and thereby prevents wearing down and damage to opposing bone surfaces. Most normal healthy articular cartilage is referred to as "hyaline," i.e., having a characteristic frosted glass appearance. Under physiological conditions, articular cartilage tissue rests on the underlying mineralized bone surface, the subchondral bone, which contains highly vascularized ossicles. These highly vascularized ossicles can provide diffusible nutrients to the overlying cartilage, but not mesenchymal stem cells.

As used herein, the term "osteogenic protein" is understood to mean any protein capable of producing, when implanted into a mammal, a developmental cascade of cellular events resulting in endochondral bore formation. The developmental cascade occurring during endochondral bone differentiation consists of chemotaxis of mesenchymal cells, proliferation of progenitor cells into chondrocytes and osteoblasts, differentiation of cartilage, vascular invasion, bone formation, remodeling, and finally marrow differentiation. True osteogenic factors capable of inducing the above-described cascade of events that result in endochondral bone formation have now been identified, isolated, and cloned. These proteins, which occur in nature as disulfide-bonded dimeric proteins, are referred to in the art as "osteogenic" proteins, "osteoinductive" proteins, and "bone morphogenetic" proteins. Osteogenic protein can be, for example, any of the known bone morphogenetic proteins and/or equivalents thereof described herein and/or in the art and includes naturally sourced material, recombinant material, and any material otherwise produced which is capable of inducing tissue morphogenesis. Osteogenic protein as defined herein also is competent to induce articular cartilage formation at an appropriate in vivo avascular locus.

As used herein, the term "carrier material" is understood to mean a material having interstices for the attachment, proliferation, and differentiation of infiltrating cells. It is biodegradable in vivo and it is biocompatible. That is, it is sufficiently free of antigenic stimuli which can result in graft rejection. Preferably, the carrier comprises insoluble material and further is formulated to have a shape and dimension when implanted which substantially mimics that of the replacement bone or cartilage tissue desired. The carrier further can comprise residues specific for the tissue to be replaced and/or derived from the same tissue type.

In a preferred embodiment, the weight ratio of osteogenic protein to carrier material preferably is within the range from about 1:1 to about 1:250,000 (e.g., from about 1 mg protein: 1 mg carrier to about 4 ng protein: 1 mg carrier) and most preferably in the range from about 1: 40 to about 1: 50,000 (e.g., from about 25 µg protein: 1 mg of carrier to about 20 ng protein: 1 mg carrier).

In one embodiment, the ionizing radiation is an electron beam. In another embodiment, gamma radiation is the preferred source of ionizing radiation. It is contemplated that any conventional gamma ray or electron beam-producing device may be used in the practice of the invention. Furthermore, the preferred dosage of ionizing radiation is provided within the range of about 0.5 to about 4.0 megarads, and most preferably within the range of about 2.0 to about 3.5 megarads, which are doses sufficient to produce the FDA required sterility assurance level of $10^{-6}$ for the devices described herein. The dosages required for obtaining a sterility assurance level of $10^{-6}$ for a particular device, however, can be determined from the *"Association for the Advancement of Medical Instrumentation Guidelines"* published in 1992, the disclosure of which is incorporated herein by reference.

In another embodiment, the insoluble carrier material comprises porous material which further can be particulate. The pores preferably have dimensions that are sufficient to permit the entry and subsequent differentiation and proliferation of migratory progenitor cells in the matrices. Alternatively, the insoluble carrier material can be fabricated by closely packing the particulate material into a shape suitable for an intended use in vivo, for example, in spanning bone defects. The porous particles or packed particles preferably have a particle size within the range of about 70 to about 850 microns and most preferably within the range of about 125 to about 450 microns. In another embodiment, the carrier material is formulated as part of an articular cartilage device. The device can be formed from devitalized cartilage tissue, or other inert, non-mineralized matrix material and osteogenic protein, and the device laid on the subchondral bone surface as a sheet. Alternatively, a formulated device can be pulverized or otherwise mechanically abraded to produce particles which can be formulated into a paste or gel as described herein for application to the bone surface.

The insoluble carrier material can comprise a non-protein-based polymer, for example, a synthetic polymer comprising polylactic acid, polybutyric acid, polyglycolic acid, and/or mixtures thereof; and/or one or more naturally derived molecules, for example, hydroxyapatite, tricalcium phosphate, collagen and mixtures thereof. Collagen currently is a preferred carrier material. A person of ordinary level of skill in the art, by judicious choice of natural and/or synthetic materials, can generate polymeric matrices that have the desired in vivo physical and chemical properties. For example, autologous collagen can be mixed with synthetic polymers, including copolymers, to produce a matrix having an enhanced in vivo biodegradation rate, and/or to improve the preferred handling qualities which make the device of the invention more easy to manipulate during implantation. For example, particulate collagen-containing devices can be combined with one or more components which serve to bind the particles into a paste-like or gel-like substance. Binding materials well characterized in the art include, for example, carboxymethylcellulose, glycerol, polyethylene-glycol and the like. Alternatively, the device can comprise osteogenic protein dispersed in a synthetic matrix which provides the desired physical properties.

The osteogenic protein useful in the methods and devices of the invention, whether naturally-occurring or synthetically prepared, is capable of inducing recruitment of accessible progenitor cells and stimulating their proliferation, inducing differentiation into chondrocytes and osteoblasts, and further inducing differentiation of intermediate cartilage, vascularization, bone formation, remodeling, and finally marrow differentiation when implanted in a mammal. The protein also is competent to induce new articular cartilage tissue formation on a subchondral bone surface, when provided in an appropriate local environment.

Preferred osteogenic proteins include, for example, homo- or heterodimers of OP-1, OP-2, BMP-2, BMP-3, BMP-4, BMP-5, BMP-6 or functional equivalents thereof. These proteins are referred to in the art as members of the "Vg/dpp" protein subfamily of the TGF-β super gene family.

In another aspect, the invention provides a method for inducing bone formation and/or articular cartilage formation in a mammal. The method comprises the steps of (a) implanting at a pre-selected locus in the mammal a terminally sterilized device of the invention and (b) permitting the device to induce the appropriate tissue formation at the preselected locus.

In another aspect, the invention provides a general procedure for producing a terminally sterilized osteogenic device suitable for implantation into a mammal. The method comprises the steps of (a) providing a biologically active osteogenic protein; (b) combining the osteogenic protein with an insoluble carrier material; and (c) exposing the combination to ionizing radiation in an amount sufficient to terminally sterilize the combination while maintaining biological activity of the protein. The process is rapid, gentle and is performed using conventional irradiation devices. The invention contemplates both the sterilization process and the sterilized products produced by the method.

BRIEF DESCRIPTION OF THE DRAWINGS

The foregoing and other objects of the invention, the various features thereof, as well as the invention itself, may be more fully understood from the following description, when read together with the accompanying drawing, in which.

DETAILED DESCRIPTION OF THE INVENTION

Figure 1:
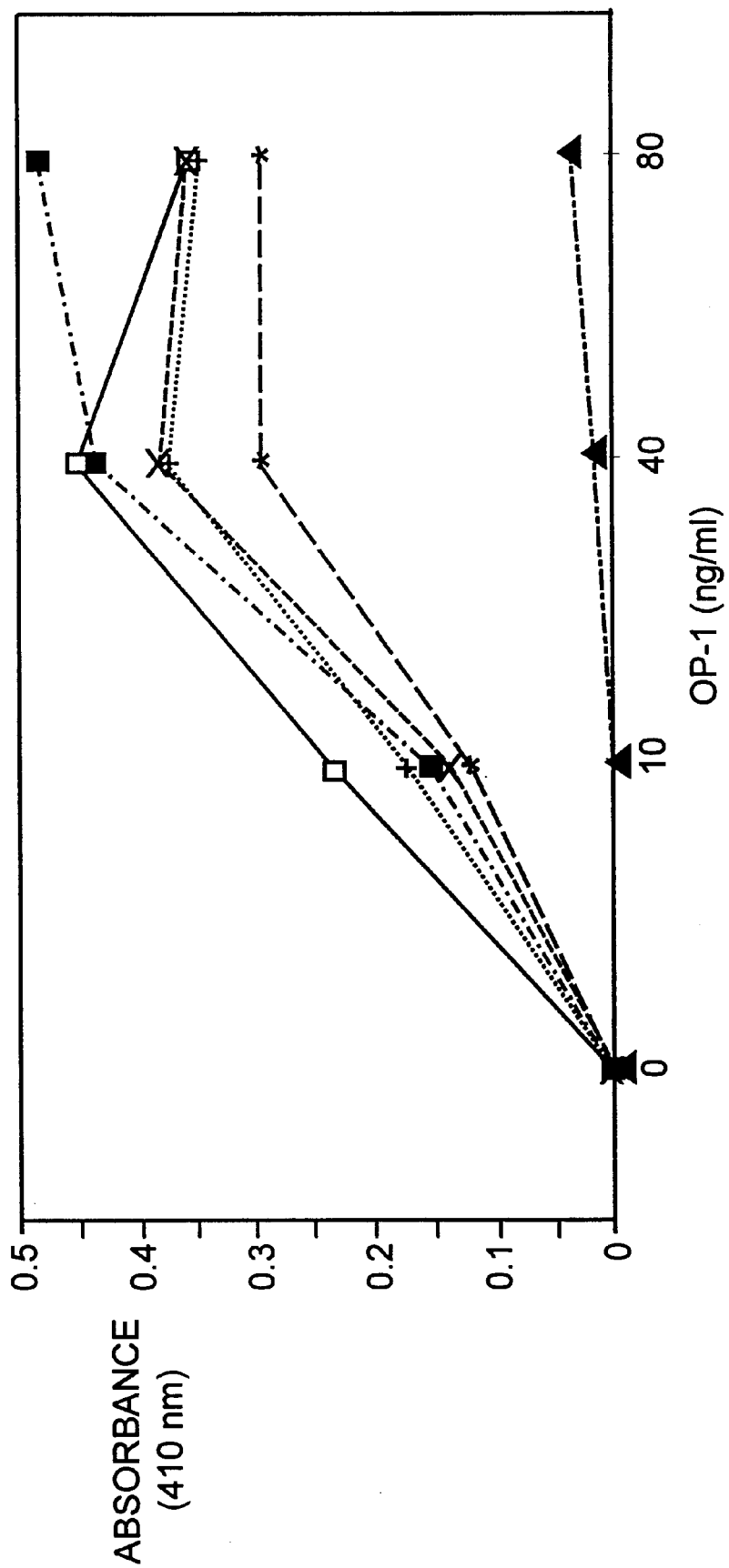
FIG. 1 is a graph depicting the ability of samples extracted from irradiated and non-irradiated osteogenic devices to stimulate alkaline phosphatase activity in a rat osteoblast cell assay. The trace having the filled triangles depicts a sample extracted from control matrix not containing OP-1; the trace having filled squares depicts a sample of untreated OP-1; the trace having crosses depicts a sample extracted from a first non-irradiated OP-1containing device; the trace having asterisks depicts a sample extracted from the first irradiated OP-1 containing device; the trace having the unfilled squares depicts a sample extracted from a second non-irradiated OP-1 containing device; and the trace having the rotated crosses depicts a sample extracted from the second irradiated OP-1 containing device.

It now has been discovered that an osteogenic device, terminally sterilized by exposure to ionizing radiation and comprising an osteogenic protein in combination with a carrier material, retains its biological activity after sterilization and is competent to induce endochondral bone formation and/or cartilage formation when implanted into a mammal. The discovery is unexpected as ionizing radiation can modify protein structure and thereby destroying biological activity.

The general procedure described herein ensures sterility of the osteogenic device while maintaining the biological activity of the osteogenic protein incorporated in the device. The procedure involves the steps of combining an insoluble carrier material and a biologically active osteogenic protein and then terminally sterilizing the combination by exposure to ionizing radiation, thereby to produce a sterile device which induces bone formation following implantation into the mammal. The method may be used for a variety of osteogenic proteins, carrier matrices and formulations thereof. The method also can be used to create devices competent to induce articular cartilage formation at an avascular site in vivo.

The preparation of terminally sterilized osteogenic devices having bone and articular cartilage forming activity in vivo, suitable osteogenic proteins, the nature and properties of the carrier material, treatments to minimize protein modification, conditions which enable terminal sterilization, and other material aspects concerning the nature and utility of the invention, including how to make and how to use the subject matter claimed herein will be further understood from the following.

I. Osteogenic Proteins

As defined herein, the osteogenic proteins useful in the composition and methods of the invention include the family of dimeric proteins having endochondral bone activity when implanted in a mammal in association with a matrix and which comprise a subclass of the "super family" of "TGF-β-like" proteins. Natural-sourced osteogenic protein in its mature, native form is a glycosylated dimer typically having an apparent molecular weight of about 30–36 kDa as determined by SDS-PAGE. When reduced, the 30 kDa protein gives rise to two glycosylated peptide subunits having apparent molecular weights of about 16 kDa and 18 kDa. In the reduced state, the protein has no detectable osteogenic activity. The unglycosylated protein dimer, which also has osteogenic activity, has an apparent molecular weight of about 27 kDa. When reduced, the 27 kDa protein gives rise to two unglycosylated polypeptides having molecular weights of about 14 kDa to 16 kDa. Useful sequences include those comprising the C-terminal 102 amino acid sequences of DPP (from Drosophila), Vgl (from Xenopus), Vgr-1 (from mouse), the OP-1 and OP-2 proteins (see U.S. Pat. No. 5,011,691), as well as the proteins referred to as BMP2, BMP3, BMP4 (see WO88/00205, U. S. Pat. No. 5,013,649 and W091/18098), BMP5 and BMP6 (see WO90/11366, PCT/US90/01630), and BMP8 and 9.

The members of this family of proteins share a conserved six or seven cysteine skeleton in the C-terminal region. See, for example, residues 335–431 of Seq. ID No. 1 in U.S. Pat. No. 5,266,6083, the disclosure of which is incorporated herein by reference, which defines the six cysteine skeleton residues referred to herein as "OPS", or residues 330–431 of Seq. ID No. 1 therein, comprising 102 amino acids which defines the seven cysteine skeleton.

This family of proteins includes longer forms of a given protein, as well as phylogenetic forms, e.g., species and allelic variants and biosynthetic mutants, including addition and deletion mutants and veriants such as those which may alter the conserved C-terminal cysteine skeleton, provided that the alteration still allows the protein to form a dimeric species having a conformation capable of inducing bone formation in a mammal when implanted in the mammal in association with a matrix. In addition, the osteogenic proteins useful in devices of this invention may include forms having varying glycosylation patterns and varying N-termini. The osteogenic proteins may be naturally occurring or biosynthetically derived, and may be produced by expression of recombinant DNA in prokaryotic or eukaryotic host cells. The proteins are active as a single species, e.g., a homodimer, or combined as a mixed species,.e.g., a heterodimer.

In one embodiment, the osteogenic protein contemplated herein comprises OP-1 or an OP-1-related sequence. Useful OP-1 sequences are recited in U.S. Pat. Nos. 5,011,691; 5,018,753 and 5,266,683; in Ozkaynak et al. (1990) *EMBO J.* 9: 2085–2093; and Sampath et al. (1993) *Proc. Natl. Acad. Sci. USA* 90: 6004–6008, the disclosures of which are incorporated herein by reference. OP-1 related sequences include xenogenic homologs, e.g.; 60A, from Drosophila, (Wharton et al. (1991) *Proc. Natl. Acad. Sci. USA* 88: 9214–9218) and proteins sharing greater than 60% identity with OP-1 in the C-terminal seven cysteine domain, preferably at least 65% identity. Examples of OP-1 related sequences include OP-2, BMP5, BMP6 and its species homolog Vgr-1 (Lyons et al. (1989) *Proc. Natl. Acad. Sci. USA* 86: 4554–4558; Celeste, et al. (1990) *Proc Natl. Acad. Sci. USA* 87: 9843–9847; and PCT international application WO93/00432; Ozkaynak et al. (1992) *J. Biol. Chem.* 267: 13198–13205). As will be appreciated by those having ordinary skill in the art, chimeric constructs can be created using standard molecular biology and mutagenesis techniques combining various portions of different morphogenic protein sequences to create a novel sequence, and these forms of the protein also are contemplated herein.

In still another preferred aspect, one or both of the polypeptide chain subunits of the osteogenically active dimer is encoded by nucleic acids which hybridize to DNA or RNA sequences encoding the active region of OP-1 under stringent hybridization conditions. As used herein, stringent hybridization conditions are defined as hybridization in 40% formamide, 5×SSPE, 5×Denhardt's Solution, and 0.1% SDS at 37° C. overnight, and washing in 0.1×SSPE, 0.1% SDS at 50° C.

Given the foregoing amino acid and DNA sequence information, the level of skill in the art, and the disclosures of numerous publications on osteogenic proteins, including U.S. Pat. No. 5,011,691 and published PCT specification US 89/01469 (published Oct. 19, 1989) various DNAs can be constructed which encode at least the active domain of an osteogenic protein useful in the devices of this invention, and various analogs thereof (including species and allelic variants and those containing genetically engineered mutations) as well as fusion proteins, truncated forms of the mature proteins, deletion and addition mutants, and similar constructs which can be used in the devices and methods of the invention. Moreover, DNA hybridization probes can be derived from fragments of any of these proteins, or designed de novo from the generic sequence defined above as OPS. These probes then can be used to screen different genomic and cDNA libraries to identify additional osteogenic proteins useful in the prosthetic devices of this invention.

The DNAs can be produced by those skilled in the art using well known DNA manipulation techniques involving genomic and cDNA isolation, construction of synthetic DNA from synthesized oligonucleotides, and cassette mutagenesis techniques. 15–100 mer oligonucleotides may be synthesized on a DNA synthesizer, and purified by polyacrylamide gel electrophoresis (PAGE) in Tris-Borate-EDTA buffer. The DNA then may be electroeluted from the gel. Overlapping oligomers may be phosphorylated by T4 polynucleotide kinase and ligated into larger blocks which may also be purified by PAGE.

The DNA from appropriately identified clones then can be isolated, subcloned (preferably into an expression vector), and sequenced. Plasmids containing sequences of interest then can be transfected into an appropriate host cell for protein expression and further characterization. The host may be a prokaryotic or eucaryotic cell since the former's inability to glycosylate protein will not destroy the protein's morphogenic activity. Useful host cells include *E. coli*, Saccharomyces, the insect/baculovirus cell system, myeloma cells, CHO cells and various other mammalian cells. The vectors additionally may encode various sequences to promote correct expression of the recombinant protein, including transcription promoter and termination sequences, enhancer sequences, preferred ribosome binding site sequences, preferred mRNA leader sequences, preferred signal sequences for protein secretion, and the like.

The DNA sequence encoding the gene of interest also may be manipulated to remove potentially inhibiting sequences or to minimize unwanted secondary structure formation. The recombinant osteogenic protein also may be expressed as a fusion protein. After being translated, the protein may be purified from the cells themselves or recovered from the culture medium. All biologically active protein forms comprise dimeric species joined by disulfide bonds or otherwise associated, produced by folding and oxidizing one or more of the various recombinant polypeptide chains within an appropriate eucaryotic cell or in vitro after expression of individual subunits. A detailed description of osteogenic proteins expressed from recombinant DNA in *E. coli* and in numerous different mammalian cells is disclosed in U.S. Pat. No. 5,266,683.

Alternatively, osteogenic polypeptide chains can be synthesized chemically using conventional peptide synthesis techniques well known to those having ordinary skill in the art. For example, the proteins may be synthesized intact or in parts on a solid phase peptide synthesizer, using standard operating procedures. Completed chains then are deprotected and purified by HPLC (high pressure liquid chromatography). If the protein is synthesized in parts, the parts may be peptide bonded using standard methodologies to form the intact protein. In general, the manner in which the osteogenic proteins are made is conventional and does not form a part of this invention.

II. Carrier Matrix Material

A. General Matrix Considerations

As will be appreciated by the skilled artisan, provided the matrix has a three dimensional structure sufficient to act as a scaffold for infiltrating and proliferating cells, and is bioresorbable biocompatible in vivo, the precise nature of the substrate per se used for the matrices disclosed herein is not determinative of a device's ultimate ability to induce new bone or articular cartilage tissue formation. In the instant invention, the substrate serves as a scaffold upon which certain cellular events, mediated by an osteogenic protein, may occur. The specific responses to the osteogenic protein ultimately are dictated by the endogenous microenvironment at the implant site and the developmental potential of the responding cells. As also will be appreciated by the skilled artisan, the precise choice of substrate utilized for the matrices disclosed herein will depend, in part, upon the type of defect to be repaired, anatomical considerations such as the extent of vascularization at the defect site, and the like.

Matrix geometry, particle size, the presence of surface charge, and the degree of porosity (cell infiltrating interstices) all are important to successful matrix performance. It is preferred to shape the matrix to the desired form of the new bone or articular cartilage tissue to be formed. Rat studies show that the new bone is formed essentially having the dimensions of the device implanted.

The matrix can comprise a shape-retaining solid made of loosely adhered particulate material e.g., with collagen. It also can comprise a molded, porous solid, or simply an aggregation of close-packed particles held in place by surrounding tissue. The matrix further can comprise an insoluble, non-particulate solid with interstices sufficient to allow the attachment and proliferation of infiltrating cells. Masticated muscle or devitalized, biologically inert tissue can be used, particularly when prepared as described herein. Large allogenic bone implants also can act as a carrier for the matrix if their marrow cavities are cleaned and packed with carrier and the dispersed osteogenic protein. Alternatively, the bone implants may act as a carrier per se and in such cases the osteogenic protein may be coated directly onto the surface of the bone implant.

Where the osteogenic device is formulated to form new bone tissue in a mammal, the currently preferred matrix material comprises devitalized, demineralized xenogenic bone tissue, treated as disclosed herein. The formulated devices produce an implantable material useful in a variety of clinical settings. In addition to its use as a matrix for bone formation in various orthopedic, periodontal, and reconstructive procedures, the matrix also can be used as a sustained release carrier, or as a collagenous coating for implants. The matrix can be shaped as desired in anticipation of surgery or shaped by the physician or technician during surgery. Thus, the material can be used for topical, subcutaneous, intraperitoneal, or intramuscular implants; it can be shaped to span a nonunion fracture or to fill a bone defect.

B. Natural-sourced Matrices

Suitable allogenic or xenogenic matrices can be created as described herein below, using methods well known in the art. Specifically, the methods are designed to extract the cellular, non-structural components of the tissue so as to devitalize the tissue. The resulting material comprises an cellular matrix defining interstices that can be infiltrated by cells and which is substantially depleted in non-structurally associated components.

A currently preferred procedure for devitalizing nonmineralized tissue follows a methodology such as that used in the art for fixing tissue. The tissue is exposed to a non-polar solvent, such as 95% ethanol, for a time sufficient to substantially replace the water content of the tissue with ethanol and to destroy the cellular structure of the tissue. Typically, the tissue is exposed to 200 proof ethanol for several days, at a temperature in the range of about 4°–40° C., taking care to replace the solution with fresh ethanol every 6–12 hours, until such time as the liquid content of the tissue comprises 70–90% ethanol. Typically, treatment for 3–4 days is appropriate. The volume of liquid added should be more than enough to submerge the tissue. The treated tissue then is lyophilized. The resulting, dry matrix is substantially depleted in non-structural components but retains both intracellular and extracellular matrix components derived from the tissue.

Treated allogenic or xenogenic matrices are envisioned to have particular utility for creating devices for forming new bone or articular cartilage in a mammal. An osteogenic device can be formulated from an allogenic bone to enhance allograft repair. Devitalized allogenic or xenogenic carrier material also can be combined with osteogenic protein to provide a solid, resorbable matrix which provides structural support for large bony defects. Similarly, an allogenic articular cartilage device can be formed from devitalized cartilage tissue, or other inert non-mineralized matrix material and osteogenic, protein, and the device laid on the subchondral bone surface as a sheet. Alternatively, a formulated device can be pulverized or otherwise mechanically abraded to produce particles which can be formulated into a paste or gel as described herein, for application to the bone surface.

C. Bone-Derived Matrices

The following provide currently preferred methodologies for creating appropriate matrices from mineralized tissue, particularly allogenic or xenogenic bone tissue.

C.1 Demineralized Bone Matrix

Demineralized bone matrix, preferably bovine bone matrix, is prepared by previously published procedures (Sampath et al. (1983) *Proc. Natl. Acad. Sci. USA* 80: 6591–6595). Bovine diaphyseal bones are obtained from a local slaughterhouse and used fresh. The bones are stripped of muscle and fat, cleaned of periosteum, demarrowed by pressure with cold water, dipped in cold absolute ethanol, and stored at −20° C. Then, they are dried and fragmented by crushing and pulverized in a large mill. Care is taken to prevent heating by using liquid nitrogen. The pulverized bone is milled to a particle size in the range of 70–850 $\mu$m, preferably 150–420 $\mu$m, and is defatted by two washes of approximately two hours duration and three volumes of chloroform: methanol (3:1). The particulate bone then is washed with one volume of absolute ethanol and dried over one volume of anhydrous ether yielding defatted bone powder. The defatted bone powder then is demineralized by four successive treatments with 10 volumes of 0.5N HCl at 4° C. for 40 min. Finally, the demineralized bone powder is neutralized by washing with a large volume of water.

C. 2. Guanidine Extraction

Demineralized bone matrix thus prepared is extracted with 5 volumes of 4M guanidine-HCl, 50 mM Tris-HCl, pH 7.0 for 16 hr at 4° C. The suspension is filtered. The insoluble material is collected and used to fabricate the matrix. The resulting material is mostly collagenous in nature and is devoid of osteogenic or chondrogenic activity.

C. 3. Matrix Treatments

The major component of all bone matrices is Type-I collagen. In addition to collagen, demineralized bone extracted as disclosed above includes non-collagenous proteins which may account for 5% of its mass. In a xenogenic matrix, these noncollageneous components may present themselves as potent antigens, and may constitute immunogenic and/or inhibitory components. These components also may inhibit osteogenesis in allogenic implants by interfering with the developmental cascade of bone differentiation. It has been discovered that treatment of the matrix particles with a collagen fibril-modifying agent extracts potentially unwanted components from the matrix, and alters the surface structure of the matrix material. Useful agents include acids, organic solvents or heated aqueous media. Various treatments are described below. A detailed physical analysis of the effect that these fibril-modifying agents have on demineralized, quanidine-extracted bone collagen particles is disclosed in copending U.S. patent application Ser. No. 483,913, filed Feb. 22, 1990.

After contact with the fibril-modifying agent, the treated matrix is washed to remove any extracted components. Briefly, the matrix is suspended in TBS (Tris-buffered saline) 1 g/200 ml and stirred at 4° C. for 2 hrs; or in 6M urea, 50 mM Tris-HCl, 500 mM NaCl, pH 7.0 (UTBS) stirred at room temperature (RT) for 30 minutes (sufficient time to neutralize the pH). The material is harvested by centrifugation, rewashed using the aforementioned conditions, and reharvested by centrifugation. The resulting material is washed with water and then lyophilized.

C. 3.1. Acid Treatments

C. 3.1a. Trifluoroacetic Acid

Trifluoroacetic acid (TFA) is a strong non-oxidizing acid that is a known swelling agent for proteins, and which modifies collagen fibrils. Bovine bone residue prepared as described above is sieved, and particles of the appropriate size are collected. These particles are extracted with various percentages (1.0% to 100%) of trifluoroacetic acid and water (v/v) at 0° C. or room temperature for 1–2 hours with constant stirring. The treated matrix is filtered, lyophilized, or washed with water/salt and then lyophilized.

C. 3.1b. Hydrogen Fluoride

Like trifluoroacetic acid, hydrogen fluoride (HF) is a strong acid and swelling agent, and also is capable of altering intraparticle surface structure. Hydrogen fluoride also is a known deglycosylating agent. As such, hydrogen fluoride may function to increase the osteogenic activity of these matrices by removing the antigenic carbohydrate content of any glycoproteins still associated with the matrix after guanidine extraction.

Bovine bone residue prepared as described above is sieved, and particles of the appropriate size are collected. The sample is dried in vacuo over $P_2O_5$, transferred to the reaction vessel and exposed to anhydrous hydrogen fluoride (10–20 ml/g of matrix) by distillation onto the sample at −70° C. The vessel is allowed to warm to 0° C. and then the reaction mixture is stirred at this temperature for 120 minutes. After evaporation of the hydrogen fluoride in vacuo, the residue is dried thoroughly over KOH pellets in vacuo to remove any remaining traces of acid. Extent of deglycosylation can be determined from carbohydrate analysis of matrix samples taken before and after treatment with hydrogen fluoride, after washing the samples appropriately to remove non-covalently bound carbohydrate. SDS-extracted protein from HF-treated material is negative for carbohydrate as determined by Con A blotting. Then, the deglycosylated bone matrix is washed twice in TBS (Tris-buffered saline) or UTBS, then washed with water and then lyophilized. Other acid treatments, however are envisioned in addition to HF and TFA.

C. 3.2 Solvent Treatment

C. 3.2a. Dichloromethane

Dichloromethane (DCM) is an organic solvent capable of denaturing proteins without affecting their primary structure. This swelling agent is a common reagent in automated peptide synthesis, and is used in washing steps to remove components. Bovine bone residue, prepared as described above, is sieved, and particles of the appropriate size are incubated in 100% DCM or, preferably, 99.9% DCM/0.1% TFA. The matrix is incubated with the swelling agent for one or two hours at 0° C. or at room temperature. Alternatively, the matrix is treated with the agent at least three times with short washes (20 minutes each) with no incubation.

C. 3.2b. Acetonitrile

Acetonitrile (ACN) is an organic solvent, capable of denaturing proteins without affecting their primary structure. It is a common reagent used in a high-performance liquid chromatography, and is used to elute proteins from silica-based columns by perturbing hydrophobic interactions. Bovine bone residue particles of the appropriate size, prepared as described above, are treated with 100% ACN (1.0 g/30 ml) or, preferably, 99.9% ACN/0.1% TFA at room temperature for 1–2 hours with constant stirring. The treated matrix is then washed with water, a urea buffer, or 4M NaCl and then lyophilized. Alternatively, the ACN or ACN/TFA treated matrix may be lyophilized without washing.

C. 3.2c. Isopropanol

Isopropanol also is an organic solvent capable of denaturing proteins without affecting their primary structure. It is a common reagent used to elute proteins from silica HPLC columns. Bovine bone residue particles of the appropriate size prepared as described above are treated with 100% isopropanol (1.0 g/30 ml) or, preferably, in the presence of 0.1% TFA, at room temperature for 1–2 hours with constant stirring. The matrix than is washed with water, urea buffer, or 4 M NaCl before being lyophilized.

C. 3.2d. Chloroform

Chloroform also may be used to increase surface area of bone matrix like the reagents set forth above, either alone or acidified. Treatment as set forth above is effective to assure that the material is free of pathogens prior to implantation.

C. 3.3 Heat Treatment

The currently most preferred agent is a heated aqueous fibril-modifying medium such as water, to increase the matrix particle surface area and porosity. The currently most preferred aqueous medium is an acidic aqueous medium having a pH of less than about 4.5, e.g., within the range of about pH 2-pH 4 which may help to "swell" the collagen before heating. 0.1% acetic acid, which has a pH of about 3, currently is most preferred. 0.1M acetic acid also may be used.

Various amounts of delipidated, demineralized guanidine-extracted bone collagen are heated in the aqueous medium (1 g matrix/30 ml aqueous medium) under constant stirring in a water jacketed glass flask, and maintained at a given temperature for a predetermined period of time. Preferred treatment times are about one hour, although exposure times of between about 0.5 to two hours appear acceptable. The temperature employed is held constant at a temperature within the range of about 37° C. to 65° C. The currently preferred heat treatment temperature is within the range of about 45° C. to 65° C.

After the heat treatment, the matrix is filtered, washed, lyophilized and used for implant. Where an acidic aqueous medium is used, the matrix also is preferably neutralized prior to washing and lypohilization. A currently preferred neutralization buffer is a 200 mM sodium phosphate buffer, pH 7.0. To neutralize the matrix, the matrix preferably first is allowed to cool following thermal treatment, the acidic aqueous medium (e.g., 0.1% acetic acid) then is removed and replaced with the neutralization buffer and the matrix agitated for about 30 minutes. The neutralization buffer then may be removed and the matrix washed and lyophilized The matrix also may be treated to remove contaminating heavy metals, such as by exposing the matrix to a metal ion chelator. For example, following thermal treatment with 0.1% acetic acid, the matrix may be neutralized in a neutralization buffer containing sodium ethylenediamietetraacetic acid (EDTA), e.g., 200 mM sodium phosphate, 5 mM EDTA, pH 7.0. 5 mM EDTA provides about a 100-fold molar excess of chelator to residual heavy metals present in the most contaminated matrix tested to date. Subsequent washing of the matrix following neutralization appears to remove the bulk of the EDTA. EDTA treatment of matrix particles reduces the residual heavy metal content of all metals tested (Sb, As, Be, Cd, Cr, Cu, Co, Pb, Hg, Ni, Se, Ag, Zn, Tl) to less than about 1 ppm. Bioassays with EDTA-treated matrices indicate that treatment with the metal ion chelator does not inhibit bone inducing activity.

The collagen matrix materials preferably take the form of a fine powder, insoluble in water, comprising nonadherent particles. It may be used simply by packing into the volume where new bone growth or sustained release is desired, held in place by surrounding tissue. Alternatively, the powder may be encapsulated in, e.g., a gelatin or polylactic acid coating, which is absorbed readily by the body. The powder may be shaped to a volume of given dimensions and held in that shape by interadhering the particles using, for example, soluble species-biocompatible collagen. The material also may be produced in sheet, rod, bead, or other macroscopic shapes.

D. Synthetic Matrices

As an alternative to a natural-sourced matrix, or as a supplement to be used in combination with a natural-sourced matrix, a suitable matrix also can be formulated de novo, using one or more materials which serve to create a three-dimensional scaffolding structure that can be formed or molded to take on the dimensions of the replacement tissue desired. Preferably, the matrix also comprises residues derived from and/or characteristic of, or specific for, the same tissue type as the tissue to be induced. In some circumstances, as in the formation of articular cartilage on a subchondral bone surface, osteogenic protein in combination with a matrix defining a three-dimensional scaffolding structure sufficient to allow the attachment of infiltrating cells and composed of a non-mineralized material can be sufficient. Any one or combination of materials can be used to advantage, including, without limitation, collagen; homopolymers or copolymers of glycolic acid, lactic acid, and butyric acid, including derivatives thereof; and ceramics, such as hydroxyapatite, tricalcium phosphate and other calcium phosphates and combinations thereof.

The tissue-specific component of a synthetic matrix readily can be obtained by devitalizing an allogenic or xenogenic tissue as described above and then pulerizing or otherwise mechanically breaking down the insoluble matrix remaining. This particulate material then can be combined with one or more structural materials, including those described herein. Alternatively, tissue-specific components can be further purified from the treated matrix using standard extraction procedures well characterized in the art and, using standard analysis procedures, the extracted material at each purification step can be tested for its tissue-specificity capability. For exemplary tissue extraction protocols, see, for example, Sampath et al. (1987) *Proc. Natl. Acad. Sci* 78: 7599–7603 and U.S. Pat. No. 4,968,590, the disclosures of which are incorporated herein by reference.

A synthetic matrix may be desirable where, for example, replacement articular cartilage is desired in an existing joint to, for example, correct a tear or limited superficial defect in the tissue, or to increase the height of the articular cartilage surface now worn due to age, disease or trauma. Such "resurfacing" of the articular cartilage layer can be achieved using the methods and compositions of the instant invention by, in one embodiment, treating a sheet of allogenic or xenogenic articular cartilage tissue as described herein, coating the resulting matrix with osteogenic protein, rolling up the formulated device so that it can be introduced to the joint using standard orthoscopic surgical techniques and, once provided to the site, unrolling the device as a layer onto the articular bone surface.

In another embodiment, the device is formulated as a paste or injectable gel-like substance that can be injected onto the articular bone surface in a joint, using standard orthoscopic surgical techniques. In this embodiment, the formulation may comprise a pulverized or otherwise mechanically degraded device comprising both matrix and osteogenic protein and, in addition, one or more components which serve to bind the particles into a paste-like or gel-like substance. Binding materials well characterized in the art include, for example, carboxymethylcellulose, glycerol, polyethylene-glycol and the like. Alternatively, the device can comprise osteogenic protein dispersed in a synthetic matrix which provides the desired physical properties.

As an example, a synthetic matrix having tissue specificity for cartilage and bone is described in WO91/18558 (published Dec. 21, 1991). Briefly, the matrix comprises a porous crosslinked structural polymer of biocompatible, biodegradable collagen and appropriate, tissue-specific glycosaminoglycans as tissue-specific cell attachment factors. Collagen derived from a number of sources can be used, including insoluble collagen, acid-soluble collagen, collagen soluble in neutral or basic aqueous solutions, as well as those collagens which are commercially available.

Glycosaminoglycans (GAGs) or mucopolysaccharides are hexosamine-containing polysaccharides of animal origin that have a tissue specific distribution, and therefore may be used to help determine the tissue specificity of the morphogen-stimulated differentiating cells. Reaction with the GAGs also provides collagen with another valuable property, i.e., inability to provoke an immune reaction (foreign body reaction) from an animal host.

Chemically, GAGs are made up of residues of hexoamines glycosidically bound and alternating in a more-or-less regular manner with either hexouronic acid or hexose moieties (see, e.g., Dodgson et al. in "Carbohydrate Metabolism and its Disorders", Dickens et al., eds. vol. 1, Academic Press (1968)). Useful GAGs include hyaluronic acid, heparin, heparin sulfate, chondroitin 6-sulfate, chondroitin 4-sulfate, dermatan sulfate, and keratin sulfate. Other GAGs also can be used for forming the matrix described herein, and those skilled in the art will either know or be able to ascertain other suitable GAGs using no more than routine experimentation. For a more detailed description of mucopolysaccharides, see Aspinall, "Polysaccharides", Pergamon Press, Oxford (1970).

Collagen can be reacted with a GAG in aqueous acidic solutions, preferably in diluted acetic acid solutions. By adding the GAG dropwise into the aqueous collagen dispersion, coprecipitates of tangled collagen fibrils coated with GAG results. This tangled mass of fibers then can be homogenized to form a homogeneous dispersion of fine fibers and then filtered and dried.

Insolubility of the collagen-GAG products can be raised to the desired degree by covalently cross-linking these materials, which also serves to raise the resistance to resorption of these materials. In general, any covalent cross-linking method suitable for cross-linking collagen also is suitable for cross-linking these composite materials, although crosslinking by a dehydrothermal process is preferred.

When dry, the cross-linked particles are essentially spherical with diameters of about 500 $\mu$m. Scanning electron microscopy shows pores of about 20 $\mu$m on the surface and 40 $\mu$m on the interior. The interior is made up of both fibrous and sheet-like structures, providing surfaces for cell attachment. The voids interconnect, providing access to the cells throughout the interior of the particle. The material appears to be roughly 99.5% void volume, making the material very efficient in terms of the potential cell mass that can be grown per gram of microcarrier.

Another useful synthetic matrix is one formulated from biocompatible, in vivo biodegradable synthetic polymer, such as those composed of glycolic acid, lactic acid and/or butyric acid, including copolymers and derivatives thereof. These polymers are well described in the art and are available commercially. For example, 50:50 mixtures of poly D,L lactide: glycolide are commercially available from Boehringer Ingelheim (e.g., RG503, RG506, RG502H and RG503H), and Birmingham Polymers (e.g., Lactel). In addition, polymers comprising 80% polylactide/20% glycoside or poly 3-hydroxybutyric acid may be purchased from PolySciences, Inc. The polymer compositions generally are obtained in particulate form and the osteogenic devices preferably fabricated under aqueous conditions in combination with an organic solvent (e.g., in an ethanol-trifluoroacetic acid solution, EtOH/TFA). In addition, one can alter the morphology of the particulate polymer compositions, for example to increase porosity, using any of a number of particular solvent treatments known in the art.

III. Fabrication of the Osteogenic Device

The naturally sourced and recombinant proteins as set forth above, as well as other constructs, can be combined and dispersed in a suitable matrix preparation using any of the methods described herein and/or in U.S. Pat. No. 5,266,683, the disclosure of which is incorporated by reference hereinabove.

Typically, osteogenic protein is dissolved in a suitable solvent and combined with the matrix. The components are allowed to associate. Typically, the combined material then is lyophilized, with the result that the osteogenic protein is disposed on, or adsorbed to the surfaces of the matrix. Useful solubilizing solvents include, without limitation, an ethanol/trifluoroacetic acid solution (e.g., 47.5% EtOH/0.01% TFA); an acetonitrile/TFA solution; ethanol; ethanol in water; or aqueous buffers. Formulations in an acidic buffer can facilitate adsorption of OP-1 onto the matrix surface. For the devices of the invention a useful formulation protocol is incubation of matrix and osteogenic protein in an ethanol/TFA solution (e.g., 30–50% EtOH/0.01–0.1% TFA) for 24 hours, followed by lyophilization. This procedure is sufficient to adsorb or precipitate 70–90% of the protein onto the matrix surface.

The quantity of osteogenic protein used will depend on the size of replacement device to be used and on the specific activity of the osteogenic protein. Greater amounts may be used for large implants. Clinical formulations for large bony defects currently comprise approximately 2.5 mg osteogenic protein per g of collagen matrix.

1. Ethanol Triflouracetic Acid Lyophilization

In this procedure, osteogenic protein is solubilized in an ethanol triflouracetic acid solution (47.5% EtOH/0.01% TFA) and added to the carrier material. The flurry is mixed and then lyophilized. This method currently is preferred.

2. Acetonitrile Trifluoracetic Acid Lyophilization

This is a variation of the above procedure, using an acetonitrile trifluoracetic (ACN/TFA) solution to solubilize the osteogenic protein that then is added to the carrier material. Samples are vigorously vortexed many times and then lyophilized.

3. Ethanol Precipitation

Matrix is added to osteogenic protein dissolved in guanidine-HCl. Samples are vortexed, incubated at a low temperature (e.g., 4° C.), and revortexed. Cold absolute ethanol (5 volumes) is added to the mixture which is then stirred and incubated, preferably for 30 minutes at −20° C. After centrifugation (microfuge, high speed) he supernatant is discarded. The reconstituted matrix is washed twice with cold concentrated ethanol in water (85% EtOH) and then lyophilized.

4. Urea Lyophilization

For those osteogenic proteins that are prepared in urea buffer, the protein is mixed with the matrix material, vortexed many times, and then lyophilized. The lyophilized material may be used "as is" for implants.

5. Buffer Lyophilization.

Osteogenic protein preparations in a physiological buffer also can be vortexed with the matrix and lyophilized to produce osteogenically active formulations.

Furthermore, the procedures described herein can be used to adsorb other active therapeutic drugs, hormones, and various bioactive species to the matrix for sustained release purposes. For example, in addition to osteogenic proteins, various growth factors, hormones, enzymes, therapeutic compositions, antibiotics, or other bioactive agents also can be adsorbed onto, or impregnated within, a substrate and released over time when implanted and the matrix slowly is absorbed. Thus, various known growth factors such as EGF, PDGF, IGF, FGF, TGF-α, and TGF-β can be released in vivo. The matrix can also be used to release chemotherapeutic agents, insulin, enzymes, enzyme inhibitors or chemotactic-chemoattractant factors.

IV. Sterilization.

Following formulation, the resulting osteogenic devices are sterilized by exposure to ionizing radiation, for example, by exposure to an election beam or to gamma irradiation. Because high energy oxygen ions and radicals may be generated from oxygen atoms associated with the device, residual air should be removed from the device prior to irradiation.

Any form of packaging may be used to hold the osteogenic device of the invention, provided hat the packaging is compatible with the sterilization process and the maintenance of sterility under storage conditions. Stoppered vials currently are the preferred packaging agents.

Sterilization is performed routinely after the device has been sealed in a vial. In the currently preferred approach, the air is evacuated from the vial by means of a vacuum prior to sealing. As an additional precaution, however, the evacuated vial can be filled with an inert gas, for example, helium, neon, argon, or nitrogen, before sealing. Alternatively, the vial can simply be purged with an inert gas prior to sealing.

The sealed devices subsequently are terminally sterilized by exposure to, for example, an electron beam or gamma irradiation. The devices can be sterilized during manufacture, i.e., as an integral inline step in the manufacturing process, or alternatively, the devices, once fabricated, can be sent to commercial sterilization services, for example, Isomedix (Northboro, MA) or RTI-Process Technology (Rockaway, N.J.) for irradiation.

The devices of the invention typically are irradiated with a dosage sufficient to provide a sterility assurance level of about $10^{-6}$, as required by the Federal Drug Administration for sterilizing biomechanical devices. The actual dosages necessary for sterilizing a particular device can readily be determined by consulting the reference text "*Association for the Advancement of Medical Instrumentation Guidelines,*" published in 1992. Guidelines are provided therein for determining the radiation dose necessary to achieve a given sterility assurance level for a particular bioburden of the device. Dosages for sterilizing devices of the invention preferably are within the range of about 0.5 to about 4.0 megarads and most preferably are within the range of about 2.0 to about 3.5 megarads.

Exemplifications

The means for making and using the osteogenic devices of the invention, as well as other material aspects concerning the nature and utility of these compositions, including how to make and how to use the subject matter claimed, will be further understood from the following which constitutes the best mode currently contemplated for practicing the invention. It will be appreciated that the invention is not limited to such exemplary work or to the specific details set forth in these examples.

EXAMPLE 1

Bioactivity of a Terminally Sterilized Osteogenic Device Comprising OP-1 and Bovine Collagen Carrier Material Demineralized, guanidine-extracted bovine matrix was formulated with increasing amounts of OP-1 using the ethanol/TFA protocol as described herein. Briefly, OP-1 solubilized in ethanol/TFA was incubated with bovine collagen carrier matrix material for 3 hours. The mixture was frozen as an OP-1/matrix slurry and dried under a vacuum. After formulation, each device was transferred to glass vials and water was added to some of the devices. Then, the devices were purged with helium for 5 minutes prior to sealing. The vials were closed with rubber septums and sealed. Samples were irradiated with 2.5 megarads of gamma irradiation under one of the following conditions: dry on dry ice, wet on dry ice, or dry at room temperature.

The resulting devices were evaluated for bone producing potential in the rat subcutaneous assay. In vivo bone induction was assayed as described by Sampath et al. (supra). Briefly, terminally sterilized devices were implanted subcutaneously into recipient rats under ether anesthesia. Male Long-Evans rats, aged 28–32 days, were used. A vertical incision (1 cm) was made under sterile conditions in the skin over the thoracic region, and a pocket prepared by blunt dissection. Approximately 25 mg of the test device was implanted deep into the pocket and the incision closed with a metallic skin clip. The day of implantation was designated as day zero of the experiment. Implants were removed on day 12. The heterotropic site permits study of bone induction without the possible ambiguities resulting from the use of orthotropic sites.

Bone inducing activity was determined biochemically by means of an alkaline phosphatase assay and calcium content of the day 12 implant. Alkaline phosphatase activity was determined spectrophotometrically after homogenization of the implant. Implants showing no bone development by histology have little or no alkaline phosphatase activity under these assay conditions. The assay is useful for quantification and obtaining an estimate of bone formation quickly after the implants are removed from the rat. Calcium content, on the other hand, is proportional to the amount of bone formed in the implant. Bone formation therefore is calculated by determining the calcium content of the implant on day 12 in rats.

Successful implants are characterized in that they exhibit a controlled progression through the stages of protein-induced endochondral bone development, including: (1) transient infiltration by polymorphonuclear leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoclasts, bone remodeling and dissolution of the implanted matrix on days twelve to eighteen; and (8) hematopoietic bone marrow differentiation in the ossicles on day twenty-one.

Histological sectioning and staining was performed to determine the extent of osteogenesis in the implants. Implants were fixed in Bouins Solution, embedded in paraffin, and cut into 6–8 $\mu$m sections. Staining with toluidine blue or hemotoxylin/eosin demonstrates clearly the ultimate development of endochondral bone. Twelve day implants are usually sufficient to determine whether the implants contain newly induced bone. The results of the assays are summarized in Tables 1 through 4 below.

TABLE 1

Device formulated with no OP-1/25 mg collagen

| | No Irradiation | dry/rm temp. | 2.5 megarads irradiation (helium purge) | |
|---|---|---|---|---|
| | | | dry/dry ice | wet/dry ice |
| $Ca^{2+}$ $\mu$g/mg tissue | 2.9 ± 1.9 (3) | 2.5 ± 2.3 (4) | 7.9 ± 9.7 (5) | 8.9 ± 8.6 (3) |
| Histology % Bone | 1.3 ± 1.1 (3) | 0 (4) | 0 (5) | 0 (3) |
| Alk. Phos. Units/mg/30 min. | 0.15 ± 0.08 (3) | 0.16 ± 0.03 (4) | 0.10 ± 0.05 (5) | 0.05 ± .02 (3) |
| weight mg (½ implant) | 96.1 ± 7.8 (3) | 48.0 ± 21.5 (4) | 65.2 ± 18.2 (5) | 81.5 ± 21.2 (3) |

TABLE 2

Device formulated with 500 mg OP-1/25 mg collagen matrix.

| | No irradiation | dry/rm temp. | 2.5 megarads irradiation (helium purge) | |
|---|---|---|---|---|
| | | | dry/dry ice | wet/dry ice |
| $Ca^{2+}$ $\mu$g/mg tissue | 27.0 ± 4 | 8.5 ± 5.8 (5) | 20.8 ± 10.8 (6) | 24.7 ± 10.0 (5) |
| Histology % Bone | 60 ± 8 (4) | 30 ± 20 (5) | 43 ± 29 (6) | 50 ± 28 (5) |
| Alk. Phos. Units/mg/30 min. | 1.02 ± 0.28 (4) | 1.00 ± 0.47 (5) | 1.15 ± 0.29 (6) | 0.93 ± .21 (5) |
| weight mg (½ implant) | 95.9 ± 11.6 (4) | 80.2 ± 17.5 (5) | 95.3 ± 22.0 (6) | 90.4 ± 29.5 (5) |

TABLE 3

Device formulated with 1000 ng OP-1/25 mg collagen matrix.

| | No irradiation | dry/rm temp. | 2.5 megarads irradiation (helium purge) | |
|---|---|---|---|---|
| | | | dry/dry ice | wet/dry ice |
| $Ca^{2+}$ $\mu$g/mg tissue | 37.0 ± 7.8 (5) | 19.9 ± 3.6 (5) | 25.3 ± 10.5 (5) | 29.6 ± 6.4 (5) |
| Histology % Bone | 64 ± 11 (5) | 52 ± 27 (5) | 47 ± 33 (5) | 46 ± 29 (5) |
| Alk. Phos. Units/mg/30 min. | 1.33 ± 0.37 (5) | 1.33 ± 0.60 (5) | 1.21 ± 0.63 (5) | 1.40 ± 0.37 (5) |
| Weight mg (½ implant) | 149.1 ± 37.8 (5) | 84.6 ± 16.7 (5) | 97.9 ± 25.0 (5) | 105.5 ± 14.2 (5) |

TABLE 4

Device formulated with 2500 ng OP-1/25 mg collagen matrix.

| Irrad. Conditions | No irradiation | dry/rm temp | 2.5 megarads irradiation (helium purge) | |
|---|---|---|---|---|
| | | | dry/dry ice | wet/dry ice |
| $Ca^{2+}$ $\mu$g/mg tissue | 44.6 ± 14.9 (5) | 29.0 ± 4.0 (5) | 25.9 ± 11.7 (5) | 46.4 ± 8.7 (5) |
| Histology % Bone | 78 ± 13 (5) | 74 ± 5 (5) | 54 ± 21 (5) | 78 ± 4 (5) |
| Alk. Phos. Units/mg/ 30 min. | 0.95 ± 0.19 (5) | 1.32 ± 0.28 (5) | 0.99 ± 0.21 (5) | 1.43 ± 0.11 (5) |
| Weight mg (½ implant) | 205.4 ± 47.5 (5) | 87.4 ± 25.5 (5) | 133.6 ± 44.1 (5) | 142.0 ± 13.2 (5) |

The data set forth in Tables 1 through 4 demonstrate that the osteogenic device can be sterilized by gamma irradiation as evidenced by the retention of biological activity of the OP-1 containing devices. A decrease in osteogenic potential was seen in some groups. In general, the highest retention of activity was noted in the wet samples irradiated on dry ice.

EXAMPLE 2

Alternative Procedures for Removing Air From Osteogenic Devices

Example 1 shows that under particular circumstances gamma irradiation may reduce the bioactivity of the irradiated device. These results may result from incomplete removal of air from the devices prior to irradiation. In an attempt to minimize the reduction of bioactivity different approaches were used to remove air from the devices prior to irradiation.

In a first method, the device containing vials were evacuated to less than 100 microns Hg using a lyophilizer and holding the vials under these conditions for 5 minutes prior to sealing. In a second method, the device containing vials were evacuated to less than 100 microns Hg in a lyophilizer, holding the samples for 5 minutes under these conditions, and then flushing the vials with helium for 2 minutes prior to sealing. The resulting samples were irradiated with 2.5 megarads of gamma irradiation and subsequently analyzed for biological activity using the rat subcutaneous assays as described in Example 1. The results are summarized in Table 5.

Damage to the carrier matrix material was assessed by extracting matrix with PBS and the absorbance of the resulting solution measured to determine the amount of solubilized protein. Selected extracts were analyzed for amino acid composition which suggested that the solubilized proteins were derived from collagen and represented between 1–2% of the starting carrier matrix material.

carrier matrix material for 3 hours. The mixture was frozen as an OP-1/matrix slurry and dried under a vacuum.

After formulation, each device was transferred to glass serum vials, the vials sealed under vacuum and sterilized with 2.5–3.0 megarads of gamma irradiation. All of the devices were formulated at 4° C. in glass formulation vessels. The results showing the extent of binding of OP-1 to the matrices and the recovery of OP-1 from irradiated and non-irradiated devices are set forth in Table 6.

TABLE 5

Effect of different approaches for removing air from the devices prior to irradition.

| Assay | μg OP-1 /25 mg carrier | Irradiation Conditons[1] | | | | |
|---|---|---|---|---|---|---|
| | | No Irrad. | Vacuum RT | Vacuum Dry Ice | Helium RT | Helium Dry Ice |
| Ca$^{2+}$ | 0 | 0 | 0 | 0 | 0 | 0 |
| μg/mg | 0.5 | 23 ± 13 | 14 ± 12 | 5 ± 4 | 4 ± 5 | 13 ± 7 |
| tissue | 2.5 | 39 ± 11 | 25 ± 18 | 23 ± 7 | 30 ± 10 | 35 ± 9 |
| Histology | 0 | 0 | 0 | 0 | 0 | 0 |
| % Bone | 0.5 | 55 ± 33 | 29 ± 33 | 45 ± 26 | 36 ± 31 | 55 ± 22 |
| | 2.5 | 93 ± 5 | 63 ± 27 | 88 ± 4 | 83 ± 22 | 96 ± 50 |
| Weight | 0 | 110 ± 84 | 150 ± 73 | 85 ± 24 | 105 ± 43 | 61 ± 34 |
| day 12 | 0.5 | 152 ± 23 | 121 ± 46 | 114 ± 46 | 99 ± 28 | 121 ± 32 |
| Implant, (mg) | 2.5 | 294 ± 91 | 193 ± 54 | 188 ± 53 | 171 ± 25 | 266 ± 31 |

[1]All the devices except the control were sterilized with 2.5 megarads of gamma irradiation.

The results indicate that devices irradiated on dry ice after purging with helium retained the highest levels of bioactivity. The results, however, indicate that 15 devices irradiated under vacuum at room temperature also exhibit significant levels of bioactivity.

EXAMPLE 3

Reproducibility of Terminally Sterilized Devices

Five lots of devices were produced using the standard formulation protocol. Briefly, OP-1 solubilized in 47.5% ethanol/0.01% TFA was incubated with bovine collagen The amount of OP-1 remaining in solution after 3 hours of incubation (prior to lyophilization of the device) was dependent on the ratio of OP-1 to carrier matrix used in the formulation; the higher the concentration of OP-1, the smaller the fraction of OP-1 bound to the matrix. When 2.5 mg OP-1 was formulated with one gram of matrix, the ratio used to formulate a device for the clinical trials, between 53 and 64% of the OP-1 was bound to the matrix after 3 hours incubation. The amount of OP-1 recovered from the device before and after sterilization is consistent from lot to lot of device, again showing the reproducibility of device production.

TABLE 6

Device formulated with OP-1.

| Device No. | mg OP-1/gm matrix | Lot size | % OP-1 bound at 3 hr | % OP-1 recovered from device[1] non-irrad. | irrad. |
|---|---|---|---|---|---|
| POO2-3,4M15D1 | 3.12 | 5 grams | 44 | 86 | 44 |
| POO3-1M15D1 | 1.25 | 1 gram | 91 | 86 | |
| POO3-1M15D2 | 2.50 | 1.5 grams | 53 | 79 | 56 |
| POO3-1M15D3 | 5.00 | 1 gram | 33 | 74 | |
| Device Lot #1 | 2.50 | 5.9 grams | 61 | 83 | 56 |

[1]Samples of each of the devices were extracted with 8 M urea, 0.3% Tween 80, 0.1 M NaCl and 50 mM Tris, pH 8.0 for 30 minutes at room temperature. Aliquots of the extracts were analyzed for OP-1 content using HPLC.

The data set forth in Examples 1–2 suggest that, under certain conditions irradiation can decrease the biological potency of device. These experiments were expanded to evaluate devices formulated at higher weight ratios of OP-1 to collagen matrix carrier material. The effects of irradiation on the biological activity of the formulated devices were evaluated in the rat subcutaneous assay. These devices were diluted with matrix, specifically, irradiated device was diluted with irradiated matrix and a non-irradiated device was diluted with non-irradiated matrix, such that 3.12 mg of OP-5 and 25 mg of matrix were implanted into the rats. The devices were diluted to avoid saturation of the assays. The results of each of the assays are set forth in Table 7. No significant difference in the biological activity of irradiated and non-irradiated device was observed.

is not due to a change in the elation position of irradiated OP-1. Samples of devices also were extracted with 2% SDS and these extracts analyzed by immunoblot and in a cellular assay. Based on Immunoblot analysis of OP-1 eluted from a device with SDS, pre- and post-irradiation, the protein pattern on the immunoblots looks substantially the same before and after irradiation, demonstrating that there is no significant physical change to the majority of the eluted OP-1 following terminal sterilization.

The OP-1 from two lots of collagen containing devices, lot numbers POO2–3M13D1 (first device) and POO2–4, 5M13D4 (second device) was extracted with 2% SDS. These extracts were assayed in a rat osteoblast enriched cell assay, where the addition of OP-1 causes an increase in alkaline phosphatase activity (FIG. 1). In both cases, the

TABLE 7

Biological Potency of Irradiated and Non-Irradiated Device.

| Lot Device | Irradiation Dose (megarads) | µg OP-1/ 25 mg matrix | Biological Activity Ca$^{2+}$ (µg/mg tissue) | Histology[2] |
|---|---|---|---|---|
| POO2-3M13D1 | 2.52–2/73 | 3.12 | 28.9 ± 4.3 (n = 6) | 6/6 |
| POO2-3M13D1 | none | 3.12 | 35.2 ± 5.3 (n = 6) | 6/6 |
| POO2-4,5M13D4 | 2.80–2.99 | 3.12 | 28.6 ± 8.9 (n = 6) | 6/6 |
| POO2-4,5M13D4 | none | 3.12 | 31.4 ± 14.1 (n = 6) | 6/6 |
| POO2-3,4M15D1 | 2.66–2.94 | 3.12 | 26.5 ± 13.0 (n = 8) | 8/8 |
| POO2-3,4M15D1 | none | 3.12 | 31.6 ± 15.4 (n = 8) | 8/8 |

[1]The irradiated OP-devices were diluted with irradiated matrix such that 3.12 µg of OP-1 and 25 mg matrix were implanted. Non-irradiated device was diluted with non-irradiated matrix. These samples were evaluated in the rat subcutaneous assay. The number of samples per assay are set forth in parentheses.
[2]The histology results are presented as number of implants with histological evidence of bone formation/total number of implants evaluated.

EXAMPLE 4

Dilution of Formulations With Additional Carrier Material

In order to further assess any changes in the biological activity of the device accompanying irradiation, additional studies were conducted in which irradiated and non-irradiated devices were diluted with irradiated matrix and non-irradiated matrix to produce final formulation concentrations of 3.1 µg OP-1/25 mg matrix and 1.5 µg OP-1/25 µg matrix.

Samples of the irradiated and non-irradiated devices were diluted with both irradiated matrix and non-irradiated matrix. The samples were evaluated using the rat subcutaneous assay and the results summarized in Table 8. The data again illustrate the biological potency of irradiated device.

An additional method for measuring changes accompanying irradiation of the device was to elute OP-1 from an irradiated device and to analyze it by HPLC, immunoblot and cellular assays. Results indicate that irradiation of the device decreases by 30–50% the amount of OP-1 which is eluted and detected by HPLC. Fractions from the HPLC were collected and analyzed by immunoblot. The post-irradiated OP-1 elutes in the same position from the HPLC as the pre-irradiation sample, thus the decrease in recovery activity of extracts from irradiated device was approximately 70% of extracts from non-irradiated controls. In addition, the recovery of OP-1 from irradiated device versus non-irradiated, as analyzed by HPLC, was 75% and 68% for device lot numbers POO2–3M13D1 and POO2–4,5M13D4, respectively.

TABLE 8

Biological Potency of Device Lot Number 1 Before and After irradiation.

| DEVICE | | MATRIX DILUENT | | µg OP-1/ 25 mg matrix[1] | Biological Activity[2] Ca$^{2+}$ µg/ mg tissue |
|---|---|---|---|---|---|
| irrad. | non-irrad. | irrad. | non-irrad. | | |
| + | | + | | 3.12 | 26.5 ± 13.0 |
| + | | | + | 3.12 | 36.3 ± 17.3 |
| | + | + | | 3.12 | 33.4 ± 7.6 |
| | + | | + | 3.12 | 31.6 ± 15.4 |
| + | | + | | 1.56 | 30.7 ± 11.9 |
| + | | | + | 1.56 | 39.5 ± 10.9 |

TABLE 8-continued

Biological Potency of Device Lot Number 1 Before and After irradiation.

| DEVICE | | MATRIX DILUENT | | μg OP-1/ 25 mg matrix[1] | Biological Activity[2] $Ca^{2+}$ μg/ mg tissue |
|---|---|---|---|---|---|
| irrad. | non-irrad. | irrad. | non-irrad. | | |
| | + | + | | 1.56 | 32.8 ± 13.0 |
| | + | | + | 1.56 | 46.5 ± 8.6 |

[1] Device was diluted with matrix to the final OP-1 concentrations outlined in this table. The device used for this experiment, Lot P002-3,4M15D1, was formulated with 3.12 mg OP-1/gram matrix.
[2] Eight replicates of each combination were evaluated in the rat subcutaneous assay. A portion of each implant was sent for histological evaluation and the remainder was worked up for $Ca^{2+}$ analysis. All of the implants (64 of 64) showed histological evidence of bone formation.

Equivalents

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A terminally sterilized osteogenic device for implantation into a mammal produced by a method comprising the steps of:
   (a) providing an osteogenic device comprising osteogenic protein 1 (OP-1) in combination with a biocompatible, biodegradable insoluble carrier material defining pores dimensioned to permit infiltration, proliferation, and differentiation of migratory progenitor cells when implanted into the mammal; and
   (b) exposing the osteogenic device of step (a) to ionizing radiation in an amount sufficient to achieve a sterility assurance factor of $10^{-6}$ thereby to produce a terminally sterilized osteogenic device which is competent to induce endochondral bone formation or articular cartilage formation in the mammal.

2. The device of claim 1, wherein the carrier material comprises tricalcium phosphate.

3. The device of claim 1, wherein the carrier material comprises hydroxyapatite.

4. The device of claim 1, wherein the carrier material comprises collagen.

5. The device of claim 4, wherein the carrier material further comprises hydroxyapatite.

6. The device of claim 4, wherein the carrier material further comprises tricalcium phosphate.

7. The device of claim 4, 3, 2, 5 or 6, further comprising carboxymethylcellulose.

8. The device of claim 1, wherein the carrier material and the OP-1 are combined in a weight ratio ranging from about 1:1 to about 250,000:1.

9. The device of claim 8, wherein the carrier material and the OP-1 combined in a weight ratio ranging from about 40:1 to about 50,000:1.

10. The device of claim 1, wherein the carrier comprises particles having a particle size within the range from about 70 to about 850 microns.

11. The device of claim 10, wherein the carrier material comprises particles having a particle size within the range from about 125 to about 450 microns.

12. The device of claim 1, wherein the ionizing radiation is gamma radiation.

13. The device of claim 12, wherein the gamma radiation is provided at a dose within the range from about 0.5 to about 4.0 megarads.

14. The device of claim 13, wherein the gamma radiation is provided at a dose within the range from about 2.0 to about 3.5 megarads.

15. The device of claim 1, wherein the terminally sterilized osteogenic device has at least about 20% of the biological activity as the osteogenic device prior to sterilization.

16. The device of claim 1, wherein the terminally sterilized osteogenic device is competent to induce articular cartilage formation at an avascular locus in the mammal.

17. A method of producing a terminally sterilized osteogenic device for implantation into a mammal, the method comprising the steps of:
   (a) providing an osteogenic device comprising osteogenic protein 1 (OP-1) in combination with a biocompatible, biodegradable, insoluble carrier material defining pores dimensioned to permit infiltration, proliferation, and differentiation of migratory progenitor cells when implanted into the mammal; and
   (b) exposing the osteogenic device of step (a) to ionizing radiation in an amount sufficient to achieve a sterility assurance factor of $10^{-6}$ thereby to produce a terminally sterilized osteogenic device which is competent to induce endochondral bone formation or articular cartilage formation in the mammal.

18. A method of inducing endochondral bone formation or articular cartilage formation in a mammal, the method comprising the steps of:
   (a) implanting at a preselected locus in the mammal, a terminally sterilized osteogenic device produced by the steps of:
      (i) providing an osteogenic device comprising osteogenic protein 1 (OP-1) in combination with a biocompatible, biodegradable, insoluble carrier material defining pores dimensioned to permit infiltration, proliferation, and differentiation of migratory progenitor cells when implanted into the mammal, and
      (ii) exposing the osteogenic device of step (i) to ionizing radiation in an amount sufficient to achieve a sterility assurance factor of $10^{-6}$ thereby to produce a terminally sterilized osteogenic device which is competent to induce endochondral bone formation or articular cartilage formation in the mammal; and
   (b) permitting the terminally sterilized osteogenic device to induce endochondral bone formation or articular cartilage formation at the preselected locus.

19. The method of claim 18, or 17, wherein the carrier material comprises collagen.

20. The method of claim 19, wherein the carrier material further comprises hydroxyapatite.

21. The method of claim 20, wherein the osteogenic device further comprises carboxymethylcellulose.

22. The method of claim 19, wherein the carrier material further comprises tricalcium phosphate.

23. The method of claim 22, wherein the osteogenic device further comprises carboxymethylcellulose.

24. The method of claim 19, wherein the osteogenic device further comprises carboxymethylcellulose.

25. The method of claim 18 or 17, wherein the carrier material comprises hydroxyapatite.

26. The method of claim 25, wherein the osteogenic device further comprises carboxymethylcellulose.

27. The method of claim 18 or 17, wherein the carrier material comprises tricalcium phosphate.

28. The method of claim 27, wherein the osteogenic device further comprises carboxymethylcellulose.

29. The method of claim 18 or 17, wherein the carrier material and the OP-1 are combined in a weight ratio ranging from about 1:1 to about 250,000:1.

30. The method of claim 29, wherein the carrier material and the OP-1 are combined in a weight ratio ranging from about 40:1 to about 50,000:1.

31. The method of claim 18 or 17, wherein the ionizing radiation is gamma radiation.

32. The method of claim 31, wherein the gamma radiation is provided at a dose within the range from about 0.5 to about 4.0 megarads.

33. The method of claim 32, wherein the gamma radiation is provided at a dose within the range from about 2.0 to about 3.5 megarads.

34. The method of claim 18 or 17, wherein the terminally sterilized osteogenic device has at least about 20% of the biological activity as the osteogenic device prior to sterilization.

* * * * *